(12) United States Patent
Jaber

(10) Patent No.: US 9,242,078 B2
(45) Date of Patent: Jan. 26, 2016

(54) CSF SHUNT VALVE

(71) Applicant: KING ABDULAZIZ UNIVERSITY, Jeddah (SA)

(72) Inventor: Hassan M. H. Jaber, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 353 days.

(21) Appl. No.: 13/867,965

(22) Filed: Apr. 22, 2013

(65) Prior Publication Data

US 2014/0316325 A1 Oct. 23, 2014

(51) Int. Cl.
*A61M 27/00* (2006.01)
*F16K 15/02* (2006.01)
*F16K 15/06* (2006.01)

(52) U.S. Cl.
CPC ........... *A61M 27/006* (2013.01); *A61M 27/002* (2013.01); *F16K 15/028* (2013.01); *F16K 15/063* (2013.01)

(58) Field of Classification Search
CPC .... F16K 15/028; F16K 15/063; A61M 27/00; A61M 27/002; A61M 27/006
See application file for complete search history.

(56) References Cited

U.S. PATENT DOCUMENTS

| | | | |
|---|---|---|---|
| 3,288,142 A | 11/1966 | Hakin | |
| 3,566,875 A | 3/1971 | Stoehr | |
| 3,738,365 A * | 6/1973 | Schulte | A61M 27/006 604/523 |
| 3,889,687 A | 6/1975 | Harris et al. | |
| 4,675,003 A | 6/1987 | Hooven | |
| 4,681,559 A | 7/1987 | Hooven | |
| 4,776,838 A | 10/1988 | Sainte-Rose et al. | |
| 4,776,839 A | 10/1988 | Doumenis | |
| 4,883,456 A | 11/1989 | Holter | |
| 5,069,663 A | 12/1991 | Sussman | |
| 5,368,556 A | 11/1994 | Lecuyer | |
| 2004/0082900 A1 | 4/2004 | Luttich | |
| 2006/0247569 A1* | 11/2006 | Bertrand | A61M 27/006 604/9 |
| 2008/0132823 A1 | 6/2008 | Rosenberg | |

FOREIGN PATENT DOCUMENTS

GB 1 301 124 12/1972

* cited by examiner

*Primary Examiner* — Leslie Deak
*Assistant Examiner* — Kai Weng
(74) *Attorney, Agent, or Firm* — Richard C. Litman

(57) ABSTRACT

The CSF shunt valve includes an elongate, hollow housing and a valve unit disposed within the housing. A plurality of exit ports are formed along the wall of the housing, and a plurality of bleeder ports are formed on the bottom of the housing. The valve unit includes at least one regulating mechanism disposed within the housing. Each regulating mechanism includes an obstructing member operatively attached to a spring. The spring is compressible within a predefined range of fluid pressure. The obstructing member compresses the attached spring in response to fluid pressure acting thereon, opening the exit ports for fluid being drained. The spring-biased obstructing members facilitate self-adjustment for drainage flow. Although arranged in series, the range limits are not continuous with subsequent springs, which safeguards against transient spikes in fluid pressure and ensures independent compression of subsequent springs in response to the predefined limits of pressure for that spring.

14 Claims, 8 Drawing Sheets

CSF SHUNT VALVE

BACKGROUND OF THE INVENTION

1. Field of the Invention

The present invention relates to medical devices, and particularly to a CSF (cerebrospinal fluid) shunt valve that is self-regulating and responsive to pressure differentials from the fluid being drained or shunted.

2. Description of the Related Art

Obstruction of cerebrospinal fluid (CSF) or its malabsorption leads to intracranial accumulation of CSF resulting in increased intracranial pressure (ICP) or hydrocephalus. This condition requires drainage or shunting of the CSF. As with many medical conditions, the ICP varies in a case-to-case basis, taking into consideration many variables, such as the individual's age, gender, medical history and the like. Generally, the ICP can vary anywhere between 0-20 mm Hg.

Typically, a sterile internal system through a catheter is used to shunt CSF into a body cavity such as the right atrium of the heart, pleural cavity or most commonly, the peritoneal cavity. An essential component to this procedure is a valve situated along the drainage catheter to prevent excessive drainage. Proper shunt selection usually requires accurate ICP measurements and a precision opening pressure valve or a programmable valve. However, the most commonly used valves are valves preset on one of the following differential pressure(s) (DP): low (<7 mmHg), medium (7-11 mmHg), or high (>11 mmHg). While functional, these valves can be subject to complications for the patient when the presumed pressure proves to be inaccurate, leading to improper performance of shunts, such as under- or over-drainage, necessitating replacement of the valve. Moreover, frequent monitoring and changes of the valve may be necessary when accounting for the potential changes in intracranial DP, especially since the pressure can change over time.

In light of the above, it would be a benefit in the medical arts to provide a valve with more universal application that regulates flow dynamically for a wide range of pressures. Thus, a CSF shunt valve solving the aforementioned problems is desired.

SUMMARY OF THE INVENTION

The CSF shunt valve includes an elongate, hollow housing and a valve unit disposed within the housing. A plurality of exit ports are formed along the wall of the housing, and a plurality of bleeder ports are formed on the bottom of the housing. The valve unit includes at least one regulating mechanism disposed in series within the housing. Each regulating mechanism includes an obstructing member operatively attached to a spring. The spring is compressible within a predefined range of fluid pressure. The obstructing member compresses the attached spring in response to fluid pressure acting thereon, opening the exit ports for fluid being drained. The spring-biased obstructing members facilitate self-adjustment for drainage flow. Although arranged in series, the range limits are not continuous with subsequent springs, which safeguards against transient spikes in fluid pressure and ensures independent compression of subsequent springs in response to the predefined limits of pressure for that spring.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
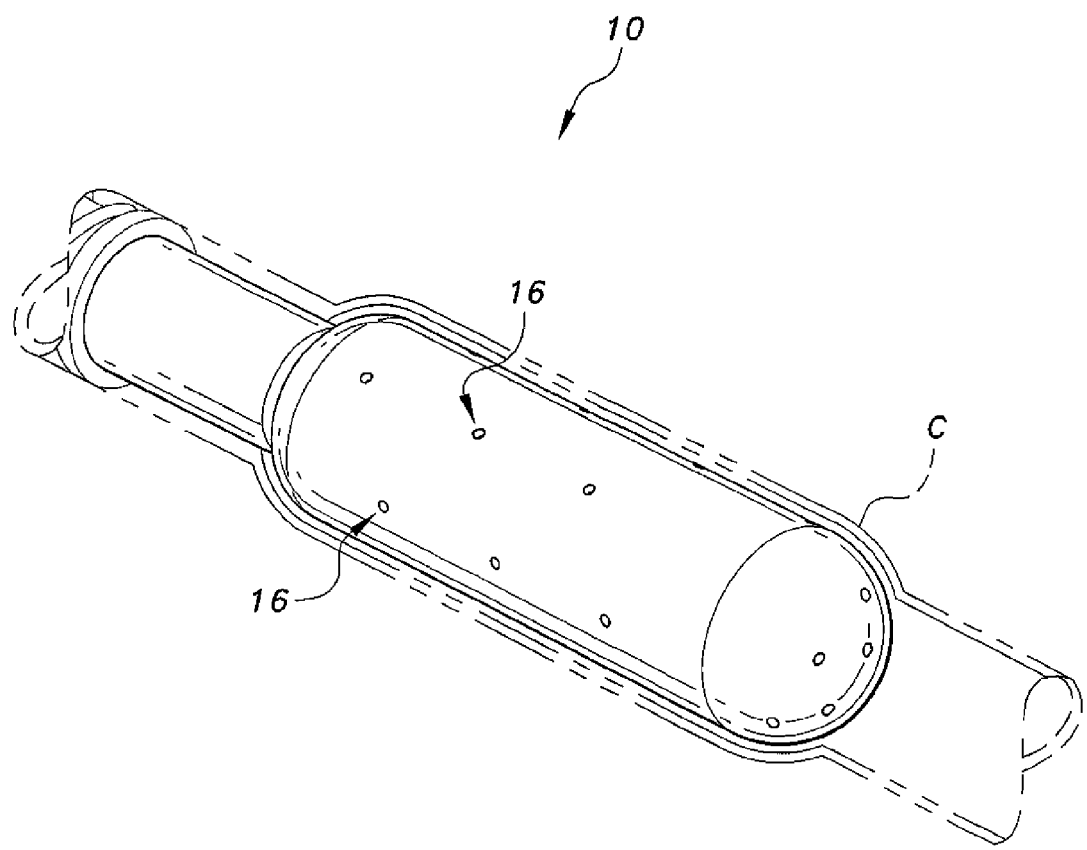
FIG. 1 is an environmental, perspective view of a CSF shunt valve according to the present invention.
Figure 2A:
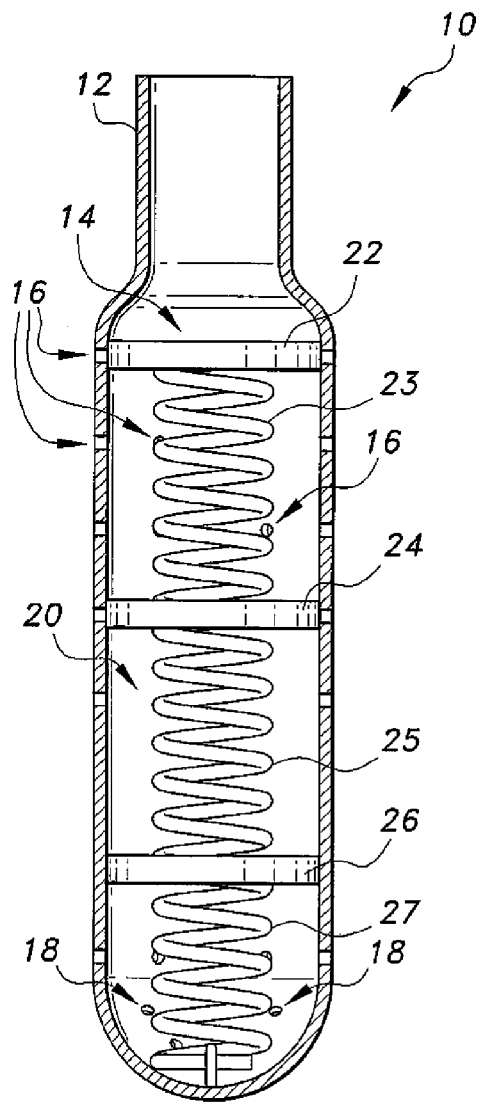
FIG. 2A is an axial section view of the CSF shunt valve of FIG. 1, shown with the flow regulating units in a fully extended position.
Figure 2B:
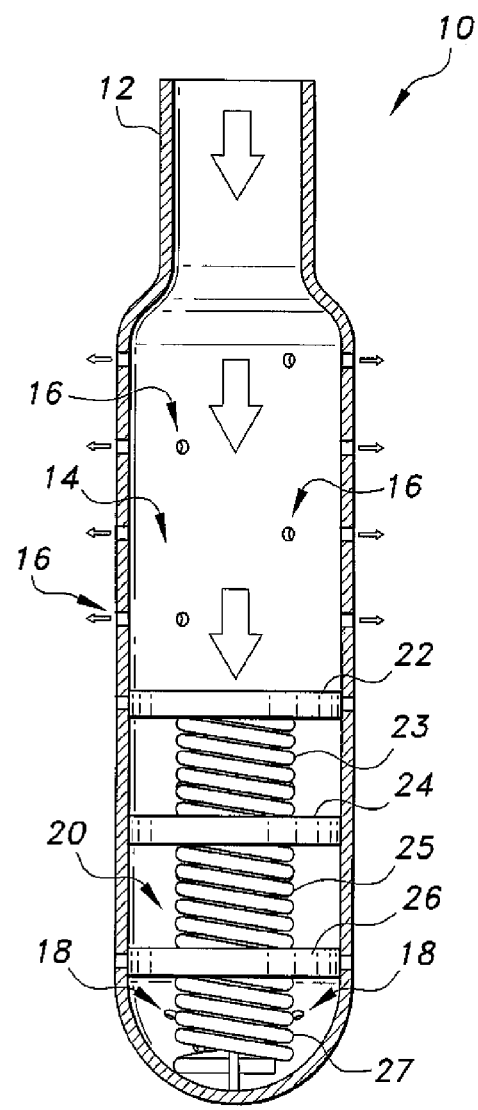
FIG. 2B is an axial section view of the CSF shunt valve of FIG. 1, shown with the flow regulating units in a compressed position.

The CSF shunt valve, a first embodiment of which is generally referred to by the reference number 10, provides self-regulating flow of CSF that varies depending upon the pressure of incoming fluid flow. As best seen in FIGS. 1, 2A and 2B, the CSF shunt valve 10 is configured to be detachably mounted to a ventricular catheter C. The CSF shunt valve 10 includes an elongate, hollow valve housing 12 defining an inner collecting chamber 14. A valve unit 20 is disposed inside the collecting chamber 14. The valve unit 20 regulates flow of CSF, while the collecting chamber 14 permits accumulation of the CSF for temporary storage and drainage through the valve unit 20.

Figure 3A:
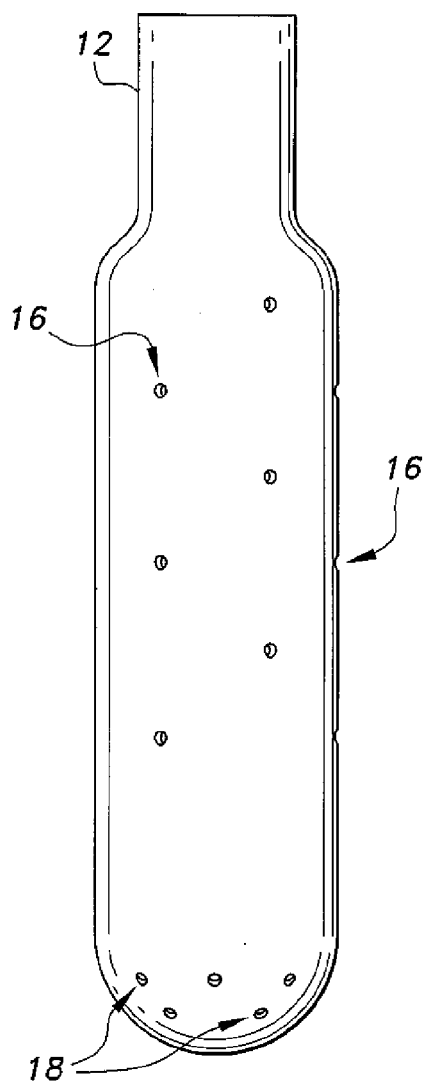
FIG. 3A is a front view of the CSF shunt valve of FIG. 1.

As best seen in FIG. 3A, the valve housing 12 is constructed as an elongate, substantially cylindrical tube having an open end for selective connection to the catheter C, the opposite end being substantially closed. A plurality of exit ports or holes 16 are formed radially in the cylindrical sidewall of the housing 12, and a plurality of bleeder ports or holes 18 are formed radially in the bottom chamber of the housing 12.

The valve unit 20 is configured as a pressure sensitive, passive means of increasing or decreasing the exit area for the incoming fluid in response to the fluid pressure acting on the valve unit 20. The valve unit 20 includes a multiple-stage mechanism for revealing the radial exit ports 16 during operation in the form of a plurality of spring-biased obstructing members, such as discs, arranged in series within the collecting chamber 14. These mechanisms can also be construed as regulating mechanisms. As best shown in FIGS. 2A and 2B, the valve 10 is constructed as a three-stage mechanism having a first disc 22, a second disc 24, a third disc 26, a first spring 23 disposed between the first disc 22 and the second disc 24 and operatively connected to both first and second discs 22, 24, a second spring 25 disposed between the second disc 24 and the third disc 26 and operatively connected to both second and third discs 24, 26, and a third spring 27 disposed between the third disc 26 and the bottom of the housing 12.

Each spring 23, 25, 27 is constructed with a spring constant designed to compress within a predetermined range of pressure acting on the valve unit 20. The first spring 23 is compressible within a range of 3-5 mmHg, the second spring 25 is compressible within a range of 7-9 mmHg, and the third spring 27 is compressible within a range of greater than 11 mmHg. These pressure ranges can be varied according to the needs of the user. Preferably, the pressure ranges for each spring are not consecutive, i.e. the pressure range from one spring to another is not continuously sequential.

The above pressure range gap between successive springs, as well as the set pressure range in the first spring 23, provides several benefits. One benefit prevents anti-siphoning of the CSF fluid being drained by forcing the pressure to be at or above the preset pressure limits prior to any movement of the discs 22, 24, 26. These pressure range gaps also permit the fluid pressure to normalize in order to resist sudden changes in transient pressure until the fluid pressure reaches or exceeds the preset pressure for the subsequent spring. The pressure requirement for the next spring in the series also provides safeguards from much higher pressure buildup. In other words, the serial arrangement of the springs 23, 25, 27 and the preselected range of pressures for each spring provide self-regulating features for controlling the pressures acting on the valve unit 20, thereby insuring efficient and optimum drainage of CSF.

In use, as the fluid enters the valve housing 12, the fluid causes pressure to build on the first disc 24. When the pressure reaches the preselected lower limit of pressures for the first spring 23, the first disc 22 begins to compress the first spring 23. Continual or sudden buildup of pressure causes the first spring 23 to be compressed further until the spring 23 is fully compressed, which occurs at or above the maximum limit of pressure for the first spring 23. Whenever the pressure reaches the minimum or is greater than the minimum pressure for the next spring 25 in the series, the second disc 24 begins to compress the second spring 25. This process repeats for the third disc 26 and third spring 27 whenever the fluid pressure is at or greater than the minimum pressure for the third spring 27. The depiction in FIG. 2A shows the valve unit 20 in the normal, fully extended position, while the depiction in FIG. 2B shows the valve unit in the fully compressed position, where CSF pressure is greater than 9 mmHg.

As the discs 24, 26, 28 progressively compress within the collecting chamber 14 in response to increasing pressure, the retracting motion of the discs 24, 26, 28 increasingly opens up more of the exit ports 16. Preferably, the number and dimensions of the radial exit ports 16 form a total exit area for the fluid being drained. This total exit area corresponds to the cross-sectional area of the lumen of the catheter C. For example, if the catheter C has a 4 mm diameter lumen, the CSF shunt valve 10 would include sixteen exit ports 16, each exit port 16 having a 1.0 mm diameter (catheter lumen has a cross sectional area of $\pi r^2 = \pi 2^2 = 12.57$ mm$^2$; each exit port has a cross-sectional area of $12.57/16 = 0.785$ mm$^2$; each exit port has a radius $r = \sqrt{A/\pi} = \sqrt{0.785/\pi} = \sqrt{0.25} = 0.5$ mm). The exit holes 16 are preferably arranged along the length of the valve housing 12 in series, spaced apart at equal distances between the normal position of the valve unit 20 (as shown in FIG. 2A) and the fully compressed position (as shown in FIG. 2B). This arrangement allows the fluid to drain through the exit ports 16 in proportion to the incoming pressure and the corresponding depressed level of the valve unit 20. Additionally, the arrangement resists over-drainage in case of increased rate of fluid egress. The plurality of bleeder ports 18 located at the bottom of the valve housing 12 allows the fluid to freely flow in and out of the collecting chamber 14, preventing air pressure between the third disc 26 and the closed end of the valve housing 12. With the above multiple stages of compressibility, it can be seen that the valve unit 20 permits dynamic self-adjustment for fluid egress, eliminating the need for constant monitoring or adjustment of the CSF shunt valve 10.

Figure 3B:
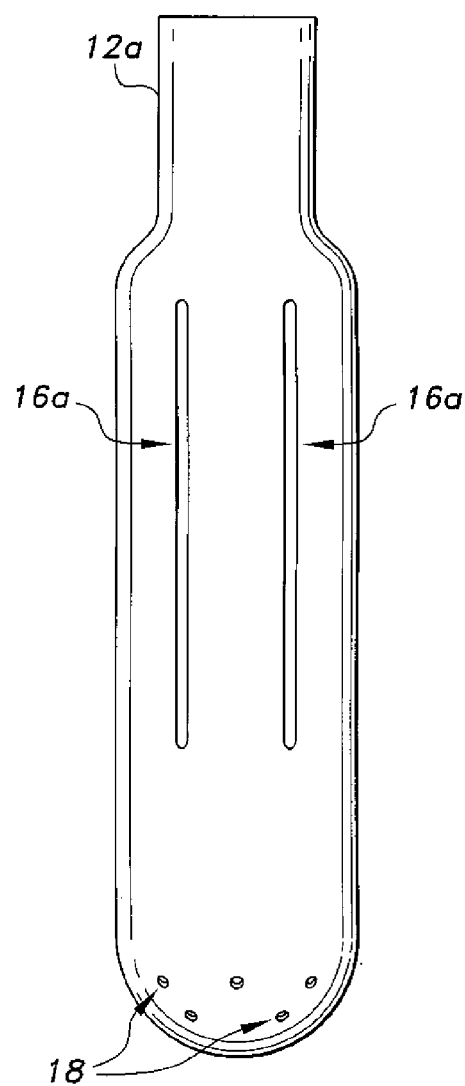
FIG. 3B is a front view of an alternative embodiment of a CSF shunt valve according to the present invention, the valve housing having slots instead of apertures.

An alternative embodiment of a CSF shunt valve having a different valve housing 12a is shown in FIG. 3B. In this embodiment, the valve housing 12a includes at least one elongate exit slot 16a formed along the length of the valve housing 12a. The exit slots 16a function the same as the plurality of exit ports 16, i.e., the fluid exit area increases the further the discs 22, 24, 26 compress due to the incoming fluid pressure. In light of this, the exit slots 16a are preferably dimensioned in a similar proportional manner as the exit ports 16 such that the total exit area thereof is equal to the total cross-sectional area of the lumen in the catheter C.

Figure 4A:
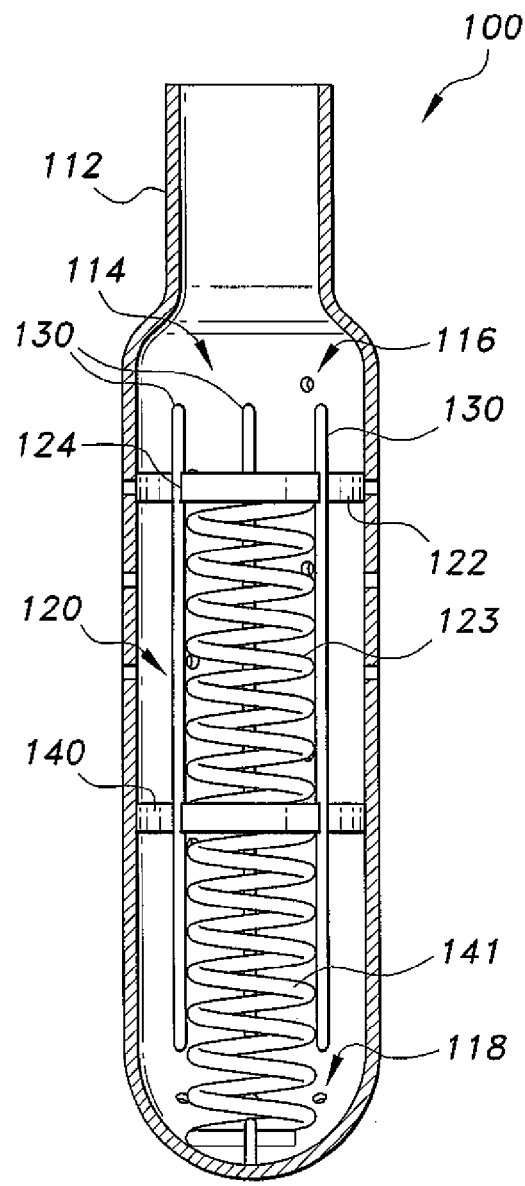
FIG. 4A is an axial section view of another alternative embodiment of a CSF shunt valve according to the present invention.
Figure 4B:
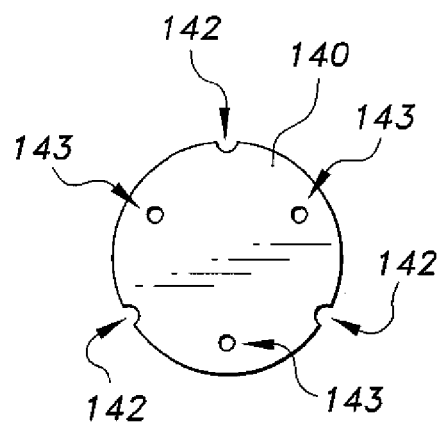
FIG. 4B is a top view of one of the disks used in the CSF shunt valve of FIG. 4A.

Another alternative embodiment of the CSF shunt valve 100 is shown in FIGS. 4A and 4B. In this embodiment, the CSF shunt valve 100 includes features for more stable operation of the valve unit 120. Much like the CSF shunt valve 10, the CSF shunt valve 100 includes an elongate, hollow valve housing 12 defining an interior collecting chamber 14; a valve unit 120; a plurality of exit ports 116 and a plurality of bleeder ports 118. However, the CSF shunt valve 100 also includes a plurality of elongate guide rails 130 disposed inside the collecting chamber 114.

The valve unit 120 includes a first disc 122 connected to a first spring 123 and a second disc 140 connected to a second spring 141, the second disc 140 and the second spring 141 being attached to the first disc 122 and the first spring 123 in series. Unlike the previous embodiment, each disc 122, 140 includes a plurality of guide notches 124, 142 formed on the periphery thereof. The notches 124, 142 are constructed to slide along the guide rails 130 so that the respective discs 122, 140 slide in a stable manner during operation, i.e., the discs 122, 140 are prevented from tilting due to the engagement between the guide notches 124, 142. Preferably, the first disc 122 is solid, providing a non-porous surface for receiving the full effect of the pressure from the incoming fluid. Any subsequent discs in the series, such as the second disc 140, can be provided with a plurality of perforations 143 that allow flow of any of the fluid flowing past the first disc 122 or accumulated within the collecting chamber 114. It is noted that while the valve unit 120 utilizes two biased discs, the CSF shunt valve 10, 100 and any of the other embodiments disclosed herein can be constructed with any number of spring-biased discs or similar constructions that provide preset compression characteristics that depend upon the incoming fluid pressure.

Figure 5A:
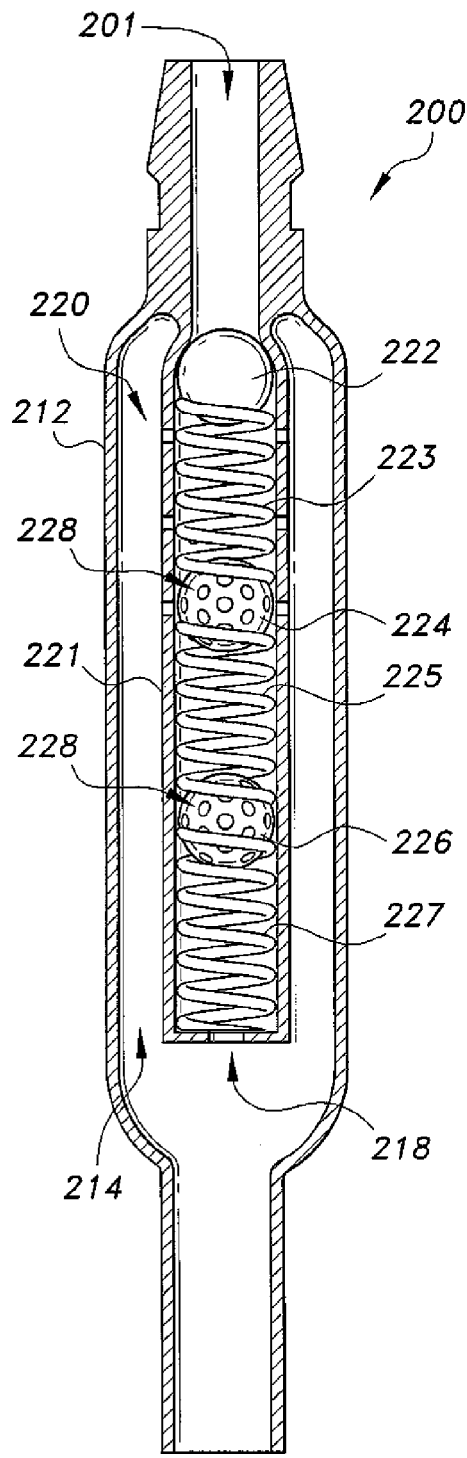
FIG. 5A is an axial section view of an alternative embodiment of a CSF shunt valve according to the present invention, shown with the flow regulating units in a fully extended position.
Figure 5B:
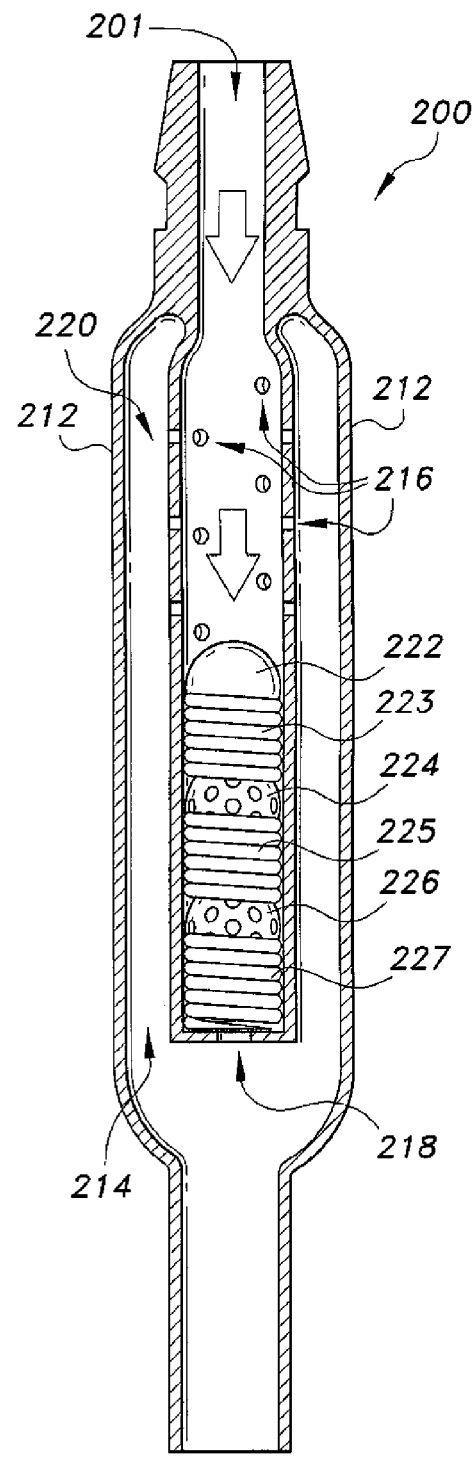
FIG. 5B is an axial section view of the CSF shunt valve of FIG. 5A, shown with the flow regulating units in a fully compressed position.

A further alternative embodiment of the CSF shunt valve 200 is shown in FIGS. 5A and 5B. In this embodiment, the valve unit 220 for the CSF shunt valve 200 incorporates spring-biased balls instead of discs. Much like the previous embodiments, the CSF shunt valve 200 includes an elongate, hollow valve housing 212 configured to be detachably mounted to a catheter C, the housing 212 defining an interior collecting chamber 214, and the valve unit 220 disposed in the collecting chamber 214.

The valve unit 220 includes an elongate, tubular sub-housing 221 integral with the fluid inlet end 201 of the housing 212. The sub-housing 221 houses a first ball 222, a first spring 223, a second ball 224, a second spring 225, a third ball 226 and a third spring 227, all operatively connected to each other in series. A plurality of exit ports 216 are formed along the wall of the sub-housing 221.

As with the previous embodiments, each ball and spring set, e.g., the first ball 222 and the first spring 223, is constructed to be compressible within a preselected range of fluid pressure. In the normal, non-draining position of the valve, all the springs 223, 225, 227 are uncompressed, and the first ball 222 blocks the inlet end 201, as best seen in FIG. 5A. When fluid is introduced through the inlet end 201 at a given pressure, the springs 223, 225, 227 serially compress in reaction to the pressure acting on the first ball 222. This reaction is substantially the same as with the biased discs in the previous embodiments. The arrangement and dimensions of the exit ports 216 provide the desired proportionate egress of fluid out of the sub-housing 221 into the collecting chamber 214. The bottom of the sub-housing 221 can include at least one bleeder port 218 permitting fluid flow between the sub-housing 221 and the collecting chamber 214. The first ball 222 is solid, while the second and third balls 224 and 226 are fenestrated to provide easier flow of fluid within the sub-housing 221.

Figure 6:
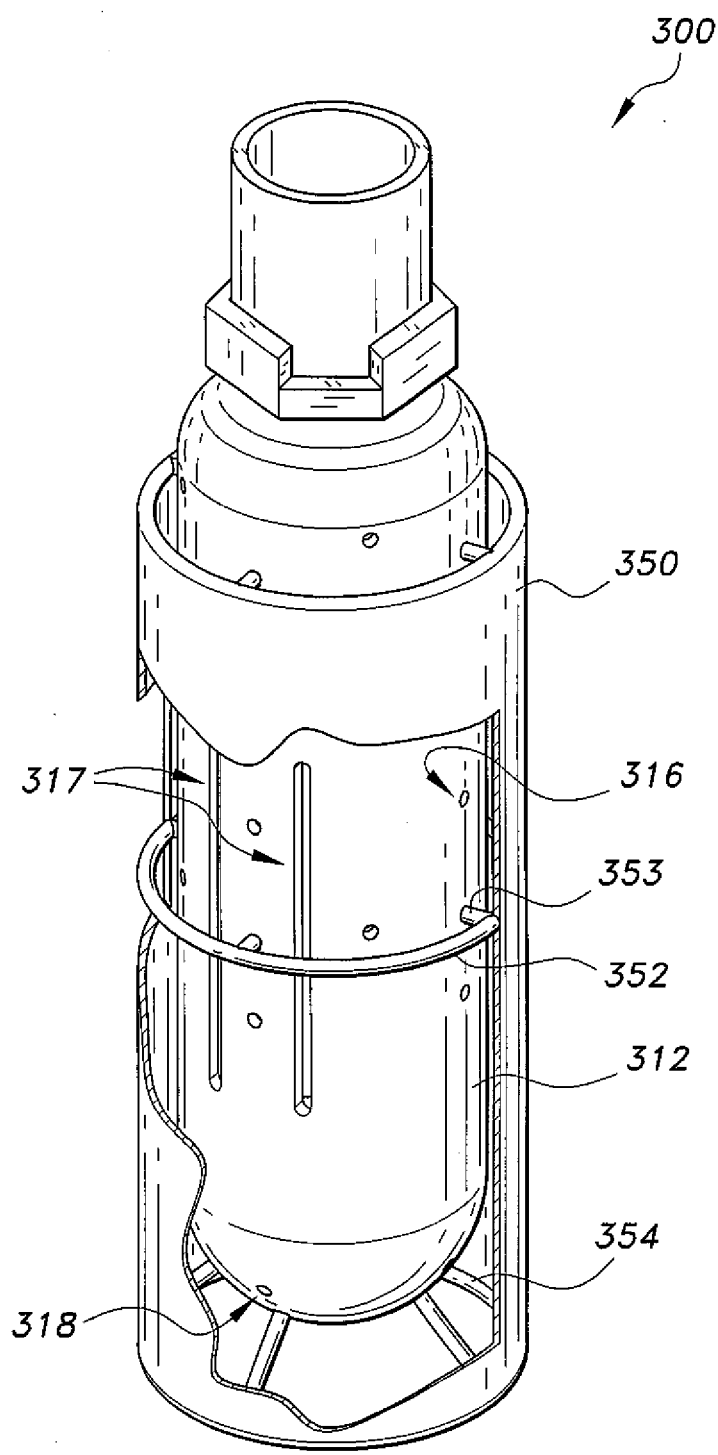
FIG. 6 is a perspective view of another alternative embodiment of a CSF shunt valve according to the present invention, shown with the protective, outer sleeve broken away and partially in section.

A still further alternative embodiment of the CSF shunt valve 300 is shown in FIG. 6. In this embodiment, the CSF shunt valve 300 is constructed to be more durable and functional, especially in times of unavoidable accidents. As shown, the CSF shunt valve 300 includes an elongate housing 312, a plurality of exit ports 316, a plurality of bleeder ports 318, and at least one elongate exit slot 317. Although not shown, any of the previously described valve units 20, 120, 220 can be provided in the housing 312. The housing 312 is reinforced and protected by an outer sleeve 350 attached to the housing 312. The outer sleeve 350 surrounds the exterior wall of the housing 312 and is dimensioned to provide an annular gap between the outer sleeve 350 and the housing 312. The outer sleeve 350 includes a plurality of reinforcing rings 352 attached to the housing 312 by a plurality of radial members or bars 353, 354. In use, the outer sleeve 350 protects the valve 300 from the environment, e.g., inadvertent impact on the valve 300 and other external hazards, while facilitating egress of fluid being drained.

Figure 7:
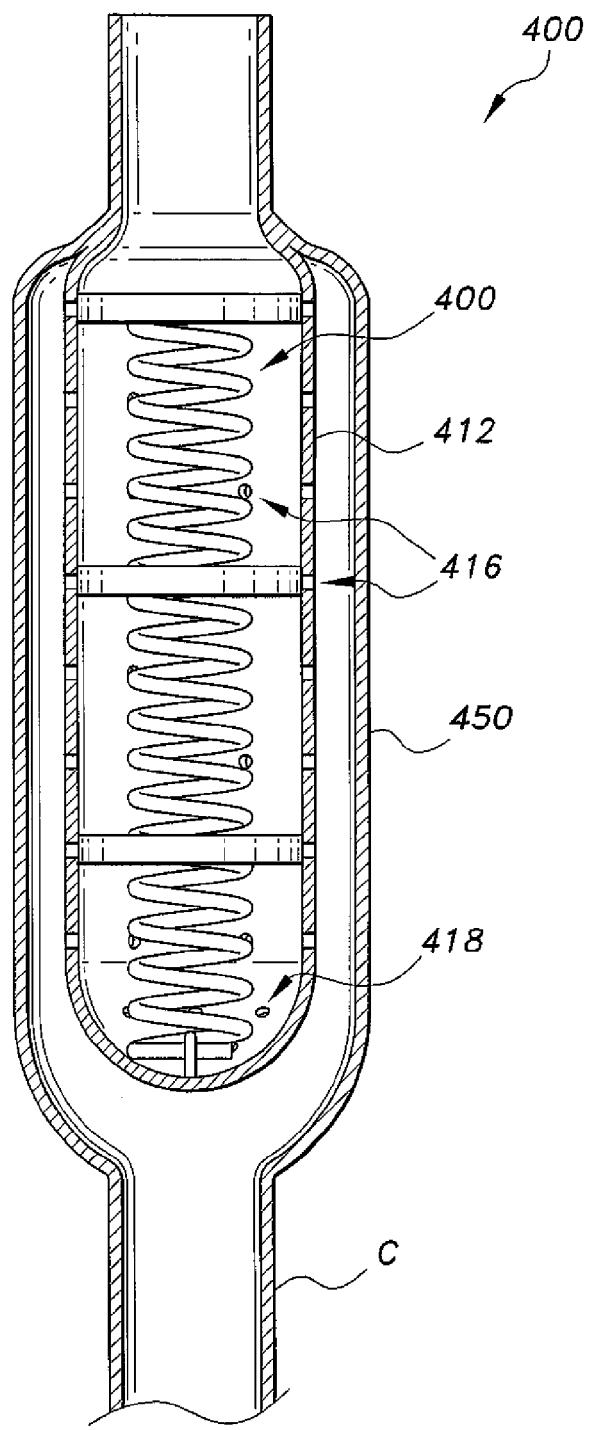
FIG. 7 is an axial section view of a further alternative embodiment of a CSF shunt valve according to the present invention.

A still further alternative embodiment of the CSF shunt valve is shown in FIG. 7. This embodiment has a catheter integrated with a CSF shunt valve according to the teachings above. As shown, the CSF shunt valve 400 includes an elongate, hollow housing 412 containing a valve unit 420 therein. A plurality of exit ports 416 and bleeder ports 418 permit drainage of incoming fluid. The housing 412 is integrally attached to or formed on a bulbous, outer drain section 450 of a catheter C. The drain section 450 surrounds the housing 412 within an interior chamber that captures the fluid being drained.

Figure 8:
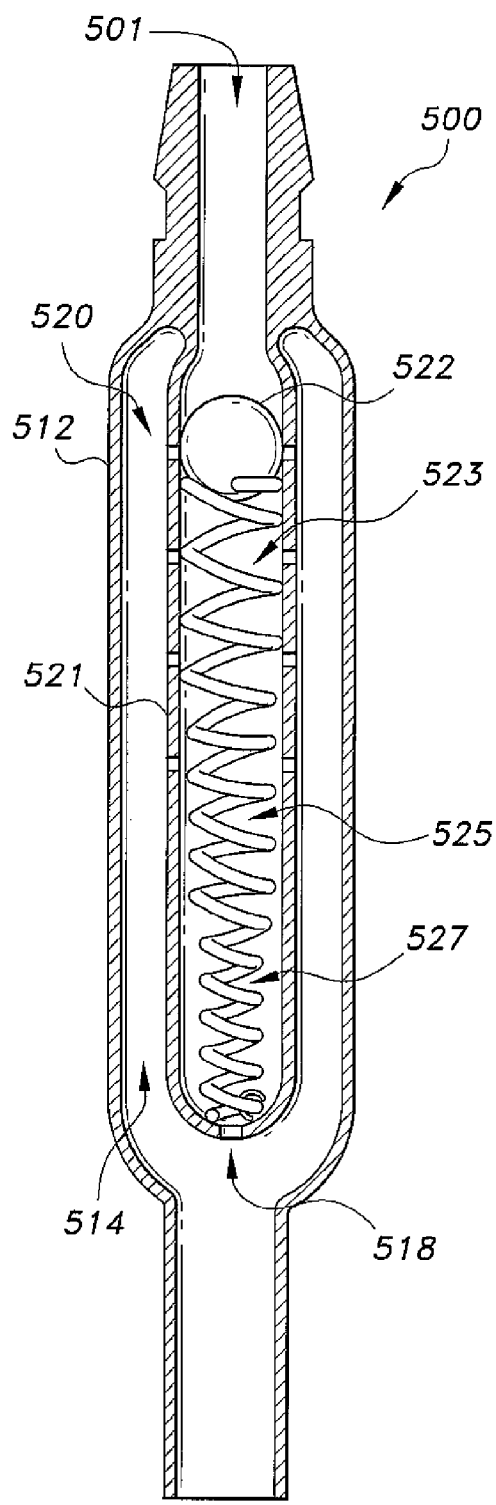
FIG. 8 is an axial section view of a still further alternative embodiment of a CSF shunt valve according to the present invention.

A still further alternative embodiment of the CSF shunt valve 500 is shown in FIG. 8. This embodiment is similar to the CSF shunt valve 200, and it is noted that similar reference numbers have been used to designate similar features. However, unlike the CSF shunt valve 200, the CSF shunt valve 500 utilizes a single ball 522 and a single spring within the tubular sub-housing 521. The ball 522 is a solid ball operatively connected to a single spring. The single spring is divided into three different, pressure-sensitive regions or sections, i.e., a first spring section 523, a second spring section 525, and a third spring section 527, representing three different stages of compressibility. Each section 523, 525, 527 is constructed to be compressible within predefined limits of fluid pressure, similar to the separate springs 223, 225, 227 in the CSF shunt valve 200, where the first spring section 523 compresses within predefined lower limits of pressure, the second spring section 525 compresses within predefined intermediate limits of pressure, and the third spring section 527 compresses within predefined higher limits of pressure. Preferably, the pressure ranges for each spring section are not consecutive, i.e. the pressure range from one spring section to another is not continuously sequential. During use, each section 523, 525, 527 compress serially in response to the pressure of the incoming CSF fluid.

It is to be understood that the CSF shunt valve 10, 100, 200, 300, 400, 500 encompasses a variety of alternatives. For example, the CSF shunt valve 10, 100, 200, 300, 400, 500 can be constructed from a variety of medical grade materials, such as plastics, metal, composites, and combinations thereof. The dimension and shape of the exit ports can be varied, so long as they provide the desired fluid flow for the drainage. Moreover, the patterned arrangement of the exit ports can be varied, so long as they provide the desired exit area corresponding to the fluid pressure. Furthermore, any of the CSF shunt valve 10, 100, 200, 300, 400 can be provided with a compressible spring having multiple stages of compressibility along progressive sections thereof similar to the single, multi-stage spring in the CSF shunt valve 500.

Various different forms of springs such as leaf springs, torsion springs, cantilevered springs and the like can also be utilized. With respect to the coil springs shown in the drawings, the coil springs can be constructed with varying length, pitch and spring constants to provide the desired compressibility as well as control thereof.

It is to be understood that the present invention is not limited to the embodiments described above, but encompasses any and all embodiments within the scope of the following claims.

I claim:

1. A CSF (cerebrospinal fluid) shunt valve, comprising:
an elongate, hollow housing adapted to be attached to a catheter having a lumen defining a cross-sectional area, the housing having a fluid inlet end, a sidewall and a bottom;
at least one exit port formed in the sidewall of the housing, the at least one exit port permitting fluid to drain through when in an open position;
at least one bleeder port formed on the bottom of the housing, the at least one bleeder port permitting the fluid to flow through the bottom of the housing; and
a valve unit disposed inside the housing, the valve unit having at least one regulating mechanism for opening the at least one exit port in response to fluid pressure acting thereon, each of the regulating mechanisms having an obstructing member blocking fluid flow through the housing and a compressible bias spring attached to the obstructing member, the compressible spring having a spring constant permitting compression of the spring within a predefined range of fluid pressure, the spring biasing the obstructing member to keep the at least one exit port in a closed position blocking fluid entering the fluid inlet end from exiting through the exit port until fluid pressure is within the predefined range, the spring being compressed to the open position when the fluid pressure is within the predefined range;
wherein the valve unit provides pressure-sensitive, self-regulating drainage of CSF fluid in response to pressure of incoming fluid;
wherein said obstructing members comprise discs;

and at least a pair of elongated guide rails disposed inside said housing each said disc having at least a pair of notches disposed along a periphery thereof, the notches on each of said discs being slidably mounted to said guide rails for stable reciprocation within said housing.

2. The CSF shunt valve according to claim 1, wherein said at least one exit port comprises an exit area equal to the cross sectional area of the catheter lumen.

3. The CSF shunt valve according to claim 1, wherein said at least one exit port comprises at least a pair of elongate exit slots extending along the length of said sidewall.

4. The CSF shunt valve according to claim 1, wherein said at least one exit port comprises a plurality of holes defined in said sidewall.

5. The CSF shunt valve according to claim 4, wherein each said hole defines an area, the total area of said holes being equal to the cross-sectional area of the catheter lumen.

6. The CSF shunt valve according to claim 4, wherein said at least one regulating mechanism comprises a plurality of regulating mechanisms, each regulating mechanism being responsive to a different range of pressure increasing in value from the inlet end to the bottom of the housing, each regulating mechanism being serially connected to each other within the housing.

7. The CSF shunt valve according to claim 6, wherein said plurality of regulating mechanisms comprises a first obstructing member, a first spring serially connected to the first obstructing member, a second obstructing member serially connected to the first spring, a second spring serially connected to the second obstructing member, a third obstructing member serially connected to the second spring, and a third spring serially connected to the third obstructing member, each spring being compressible within a different fluid pressure range, the fluid pressure range for each of the springs being discontinuous with the adjacent spring.

8. The CSF shunt valve according to claim 7, wherein said first spring is compressible within a range of about 3-5 mm Hg, said second spring is compressible within a range of about 7-9 mm Hg, and said third spring is compressible within a range of 11 mm Hg and above.

9. The CSF shunt valve according to claim 1, wherein at least one of said discs is solid.

10. The CSF shunt valve according to claim 9, wherein at least one of said discs includes at least one hole defined therein.

11. The CSF shunt valve according to claim 1, further comprising an elongate, outer sleeve surrounding and protecting said housing, said outer sleeve having a plurality of reinforcing annular rings disposed along the length of the outer sleeve, each of the rings having a plurality of members extending radially inward and attached to said housing.

12. The CSF shunt valve according to claim 1, wherein said compressible bias spring comprises a plurality of consecutive spring sections, each spring section having a spring constant different from each other, each spring section permitting compression of the spring within a predefined range of fluid pressure, said range of pressure for each of the spring sections being different and discontinuous with the adjacent spring section.

13. A CSF shunt valve, comprising:
an elongate, hollow housing adapted to be attached to a catheter, the housing having a sidewall and a bottom;
a plurality of exit ports formed in the sidewall of the housing, the exit ports permitting fluid to drain through;
a plurality of bleeder ports formed on the bottom of the housing, the plurality of bleeder ports permitting the fluid to flow through the bottom of the housing; and
a valve unit disposed inside the housing, the valve unit having at least one regulating mechanism for opening the at least one exit port in response to fluid pressure acting thereon, each of the regulating mechanisms having an obstructing member blocking fluid flow through the housing and a compressible bias spring attached to the obstructing member, the compressible spring having a spring constant permitting compression of the spring within a predefined range of fluid pressure, the spring biasing the obstructing member to keep the at least one exit port in a closed position blocking fluid entering the fluid inlet end from exiting through the exit port until fluid pressure is within the predefined range, the spring being compressed to the open position when the fluid pressure is within the predefined range, the range of pressure for each of the springs being different and discontinuous with the adjacent spring;
wherein the valve unit provides pressure-sensitive, self-regulating drainage of CSF fluid in response to pressure of incoming fluid;
wherein said obstructing members comprise discs;
and at least a pair of elongated guide rails disposed inside said housing each said disc having at least a pair of notches disposed along a periphery thereof, the notches on each of said discs being slidably mounted to said guide rails for stable reciprocation within said housing.

14. A CSF shunt valve, comprising:
an elongate, hollow housing adapted to be attached to a catheter, the housing having a sidewall and a bottom;
a plurality of exit ports formed in the sidewall of the housing, the exit ports permitting fluid to drain through;
a plurality of bleeder ports formed on the bottom of the housing, the plurality of bleeder ports permitting the fluid to flow through the bottom of the housing; and
a valve unit disposed inside the housing, the valve unit having at least one regulating mechanism for opening the at least one exit port in response to fluid pressure acting thereon, each regulating mechanism having an obstructing member blocking fluid flow through the housing and a compressible bias spring attached to the obstructing member, the compressible spring having a plurality of consecutive spring sections, each spring section having a spring constant different from each other, each spring section permitting compression of the spring within a predefined range of fluid pressure, the spring biasing the obstructing member to keep the at least one exit port in a closed position blocking fluid entering the fluid inlet end from exiting through the exit port until fluid pressure is within the predefined range of each spring section, the spring being compressed to the open position when the fluid pressure is within the predefined range of each spring section, the range of pressure for each of the spring sections being different and discontinuous with the adjacent spring section;
wherein the valve unit provides pressure-sensitive, self-regulating drainage of CSF fluid in response to pressure of incoming fluid;
wherein said obstructing members comprise discs;
and at least a pair of elongated guide rails disposed inside said housing each said disc having at least a pair of notches disposed along a periphery thereof, the notches on each of said discs being slidably mounted to said guide rails for stable reciprocation within said housing.

* * * * *